United States Patent
Yamagaito et al.

(12) 
(10) Patent No.: US 10,352,937 B2
(45) Date of Patent: Jul. 16, 2019

(54) PRETREATMENT METHOD OF SAMPLE FOR DETECTING HBS ANTIGEN AND USE THEREOF

(71) Applicant: SYSMEX CORPORATION, Kobe-shi, Hyogo (JP)

(72) Inventors: Takahiro Yamagaito, Kobe (JP); Takuya Koma, Kobe (JP); Mari Maruki, Kobe (JP); Kazuhiko Takeda, Yao (JP)

(73) Assignee: SYSMEX CORPORATION, Kobe-shi, Hyogo (JP)

(*) Notice: Subject to any disclaimer, the term of this patent is extended or adjusted under 35 U.S.C. 154(b) by 505 days.

(21) Appl. No.: 14/809,432

(22) Filed: Jul. 27, 2015

(65) Prior Publication Data

US 2015/0330982 A1    Nov. 19, 2015

Related U.S. Application Data

(63) Continuation of application No. PCT/JP2014/051701, filed on Jan. 27, 2014.

(30) Foreign Application Priority Data

Jan. 28, 2013 (JP) ................. 2013-013167

(51) Int. Cl.
*A61K 39/00* (2006.01)
*G01N 33/576* (2006.01)

(52) U.S. Cl.
CPC ..... *G01N 33/5764* (2013.01); *G01N 33/5761* (2013.01); *G01N 2333/02* (2013.01); *G01N 2469/10* (2013.01)

(58) Field of Classification Search
None
See application file for complete search history.

(56) References Cited

U.S. PATENT DOCUMENTS

| | | | |
|---|---|---|---|
| 2008/0193916 A1* | 8/2008 | Maki | C07K 14/005 435/5 |
| 2009/0280474 A1 | 11/2009 | Martin et al. | |
| 2010/0136520 A1 | 6/2010 | Coleman et al. | |
| 2011/0274786 A1 | 11/2011 | Sorensen et al. | |

FOREIGN PATENT DOCUMENTS

| | | |
|---|---|---|
| EP | 1 752 768 A1 | 2/2007 |
| EP | 2 327 987 A2 | 6/2011 |
| JP | 8-050133 A | 2/1996 |
| JP | 11-108932 A | 4/1999 |
| JP | 2009-074852 A | 4/2009 |
| JP | 2011-112631 A | 6/2011 |
| JP | 2011-520124 A | 7/2011 |
| JP | 2011-200136 A | 10/2011 |
| JP | 2012-514989 A | 7/2012 |
| WO | 2004/038417 A1 | 5/2004 |
| WO | 2006/033368 A | 3/2006 |

OTHER PUBLICATIONS

International Search Report for PCT/JP2014/051701 dated Apr. 22, 2014.
Communication dated Sep. 26, 2016, from the European Patent Office in counterpart European application No. 14743526.7.

* cited by examiner

*Primary Examiner* — Agnieszka Boesen
(74) *Attorney, Agent, or Firm* — Sughrue Mion, PLLC (57) ABSTRACT

The present invention relates to a pretreatment method of a sample for detecting HBs antigen, which is a surface antigen of the hepatitis B virus, and a method for detecting HBs antigen utilizing the pretreatment method. The present invention also relates to a pretreatment reagent kit for detecting HBs antigen.

23 Claims, 2 Drawing Sheets

PRETREATMENT METHOD OF SAMPLE FOR DETECTING HBS ANTIGEN AND USE THEREOF

CROSS-REFERENCE TO RELATED APPLICATION

This application is a continuation of International Application PCT/JP2014/051701 filed on Jan. 27, 2014, which claims benefit of Japanese patent application JP 2013-013167 filed on Jan. 28, 2013, both of which are incorporated herein by reference in their entireties.

BACKGROUND OF THE INVENTION

The present invention relates to a pretreatment method of a sample for detecting HBs antigen, which is a surface antigen of the hepatitis B virus, and a method for detecting HBs antigen utilizing the pretreatment method. The present invention also relates to a pretreatment reagent kit for detecting HBs antigen.

Hepatitis B is a liver disease caused by the hepatitis B virus (HBV). HBV is a spherical virus which is mainly composed of an envelope portion and a core portion. The envelope portion contains HBs antigen and the core portion contains genomic DNA, HBc antigen, HBe antigen and the like. After infection with HBV, HBs antigen is released into the circulation of the host and the amount thereof increases with development of hepatitis. Therefore in the test for hepatitis B, blood HBs antigen is first measured. A positive test result for HBs antigen indicates that the subject is infected with HBV. In contrast, the result of HBs antigen negative indicates that the subject is not infected with HBV. Meanwhile after onset of hepatitis B, HBs antibody is started to be produced in vivo in the host, that is a neutralizing antibody of HBs antigen. In the test for hepatitis B, infection history of the subject can be examined by simultaneously measuring HBs antibody. It is considered clinically that hepatitis B is cured when a subject is HBs antigen negative and HBs antibody positive.

However, recent studies have revealed that even after remission of hepatitis B, some HBV genes remain in liver and peripheral mononuclear cells. It has also recently been shown that application of an immunosuppressant to patients with malignant tumor or rheumatoid patients who have HBV infection history causes HBV reactivation and thus severe hepatitis. This type of hepatitis is referred to as "de novo hepatitis B" and is found to be highly frequently fulminated and have high mortality compared to normal hepatitis B.

It is considered that in order to prevent de novo hepatitis B from being fulminated, initiation of treatment at an early stage of the onset is effective. Therefor it is important to detect reactivation of the virus at the early stage. However, it is considered that at the early stage of reactivation the amount of the HBV virus is still minute and HBs antibody from a patient also exists. As HBs antibody from patients binds to HBs antigen to inhibit the detection of the antigen, a test having extremely high sensitivity is required for early detection of reactivation of HBV.

A known test of HBV with high detection sensitivity utilizes PCR. In the test, HBV DNA is amplified to detect the HBV. However, the test is generally and mostly carried out at institutions that can carry out the test after sending samples to the institutions, and thus it takes long time to have the test result available. In addition, the test is expensive.

Meanwhile a HBs antigen test by immunological means requires a short time to have the test result available compared to the test by PCR and is inexpensive. A method for detecting HBs antigen by immunological means is disclosed in WO 2006/033368, for example, in which a sample is pretreated with a denaturing agent such as an alkaline agent or a surfactant to denature HBs antibody from a patient followed by detection of HBs antigen using a certain anti-HBs antibody for detection.

SUMMARY OF THE INVENTION

In a method for detecting HBs antigen in a sample by immunological means, HBs antibody from a subject is required to be preliminarily inactivated because the antibody inhibits the detection of HBs antigen. In the method disclosed in WO 2006/033368, for example, it is described that 0.25 to 1 N of sodium hydroxide as the concentration during denaturation of HBs antibody from a patient is efficient. However, sodium hydroxide may act on HBs antigen to denature the same, resulting in loss of antigenicity of the antigen and reduction in detection sensitivity of the HBs antigen.

In order to detect HBs antigen from a sample which contains a minute amount of the antigen and may contain HBs antibody derived from a subject such as a sample at an early stage of reactivation of HBV, a method is required which does not substantially deteriorate antigenicity of HBs antigen, denatures HBs antibody derived from a subject and allows detection of HBs antigen with high sensitivity.

The inventors of the present invention have surprisingly found that treating a sample containing HBs antigen and HBs antibody from a subject with an alkaline substance at a final concentration as extremely low as 0.012 to 0.15 N allows detection of the HBs antigen with high sensitivity without substantially being affected by HBs antibody from a subject. Thus the inventors have completed the present invention.

Namely the present invention provides a pretreatment method of a sample for detecting HBs antigen, comprising the steps of:

treating a sample suspected to contain the HBs antigen by mixing the sample with a pretreatment solution containing an alkaline substance, so that a final concentration of the alkaline substance is 0.012 to 0.15 N; and neutralizing the sample obtained from the treatment step with a reagent containing an acidic substance.

The present invention also provides a method for detecting HBs antigen, comprising the steps of:

treating a sample suspected to contain the HBs antigen by mixing the sample with a pretreatment solution containing an alkaline substance, so that a final concentration of the alkaline substance is 0.012 to 0.15 N;

neutralizing the sample obtained from the treatment step with a reagent containing an acidic substance;

adding to the sample obtained from the neutralizing step a labeled antibody binding to the HBs antigen, carrier particles and a first antibody binding to the HBs antigen and the carrier particles, in order to form a complex of the HBs antigen, the labeled antibody and the first antibody on the carrier particles;

selectively recovering the carrier particles in the sample obtained from the step of formation of the complex;

transferring the complex onto a solid phase other than the carrier particles by releasing the complex from the carrier particles obtained from the step of recovering;

measuring a label of the labeled antibody in the complex on the solid phase obtained from the transfer step; and detecting the HBs antigen in the sample suspected to contain the HBs antigen on the basis of a result from the measuring step.

The present invention further provides a pretreatment reagent kit for detecting HBs antigen, which comprises a first reagent containing an alkaline substance and a second reagent containing an acidic substance at an amount sufficient for neutralizing the alkaline substance.

DETAILED DESCRIPTION OF THE EMBODIMENTS

As used herein, the term "pretreatment" intends processing, before subjecting a sample suspected to contain HBs antigen to detection of the antigen, of the sample so as to make the sample suitable for the detection. The pretreatment method of a sample of the present invention may be performed by carrying out the "treatment step" and the "neutralizing step" described hereinafter manually or by carrying out the "treatment step" manually and the "neutralizing step" in an instrument.

In the pretreatment method of a sample of the present invention (hereinafter also referred to as the "pretreatment method"), a step (hereinafter also referred to as the "treatment step") of treating a sample suspected to contain HBs antigen by mixing the sample with a pretreatment solution containing an alkaline substance, so that the final concentration of the alkaline substance is 0.012 to 0.15 N is carried out. In the treatment step, HBs antibody in a sample is denatured and inactivated by the action of the alkaline substance in the pretreatment solution.

The final concentration of the alkaline substance in the treatment step is not particularly limited as far as it is within the above-mentioned range. Examples of the final concentration include, for example, 0.012, 0.013, 0.014, 0.015, 0.016, 0.017, 0.018, 0.019, 0.020, 0.030, 0.040, 0.050, 0.060, 0.070, 0.080, 0.090, 0.10, 0.11, 0.12, 0.13, 0.14 and 0.15 N.

A sample suspected to contain HBs antigen is not particularly limited as far as it is a biological sample or a sample prepared from a biological sample. Examples of the biological sample include tissue, cells, body fluid, a secretion and excrement, and specifically include whole blood, plasma, serum, lymph fluid, bone marrow aspirate, bile, a gastrointestinal secretion, semen, saliva, breast milk, urine, feces and the like. Examples of the sample prepared from a biological sample include a dilution, a suspension, an extract and a homogenate of a biological sample including, for example, an extract of tissue or cells and a homogenate of tissue or cells.

In an embodiment of the present invention, an alkaline substance in the pretreatment solution is preferably a strong base well known in the art. Such a strong base can be at least one selected from hydroxides, hydrides and amides of alkali metals and alkaline earth metals. Among these, sodium hydroxide, potassium hydroxide and magnesium hydroxide are particularly preferred.

The concentration of the alkaline substance in the pretreatment solution is not particularly limited as far as the concentration is such that when the pretreatment solution is mixed with a sample suspected to contain HBs antigen, the final concentration of the alkaline substance is 0.012 to 0.15 N. Therefore when a sample is liquid, the concentration of the alkaline substance in the pretreatment solution can be appropriately selected according to the mixing ratio (volume ratio) of the sample and the pretreatment solution. For example, when a sample and a pretreatment solution are mixed at a volume ratio of 1:1, the concentration of the alkaline substance in the pretreatment solution may be 0.024 to 0.3 N. In an embodiment of the present invention, the mixing ratio of a sample in the form of liquid and a pretreatment solution is not particularly limited and is preferably 1:1 to 1:0.5 as a volume ratio.

In an embodiment of the present invention, it is preferable that the pretreatment solution further contains a nonionic surfactant in order to remove the HBs antibody inactivated by the action of the alkaline substance and/or other contaminants. Such a nonionic surfactant is not particularly limited and is selected from well-known polyoxyethylene nonionic surfactants. Examples of the polyoxyethylene nonionic surfactant include polyoxyethylene alkyl ether (Brij® 35, Brij® 45 and the like), polyoxyethylene alkyl phenyl ether (Triton® X-100, Triton® X-114, NP-40® and the like), polyoxyethylene sorbitan fatty acid ester (Tween®-20, Tween®-80 and the like) and the like. At least one of the foregoing may be used. Among these, polyoxyethylene alkyl ether is particularly preferred.

The concentration of the nonionic surfactant in the pretreatment solution is not particularly limited and it is desirable that the concentration is such that when the pretreatment solution is mixed with a sample, HBs antigen is not substantially denatured. For example, when the pretreatment solution contains Brij® 35, the concentration thereof is such that when the pretreatment solution is mixed with a sample, the final concentration of Brij® 35 is 0.05 to 0.5%.

In an embodiment of the present invention, it is preferable that the pretreatment solution further contains a chaotropic agent in order to remove the HBs antibody inactivated by the action of the alkaline substance and/or other contaminants. The chaotropic agent as used herein is a substance that can unstabilize the molecular structure of a protein. Such a chaotropic agent is not particularly limited and examples thereof include urea, guanidine hydrochloride, sodium salicylate, sodium thiocyanate, sodium perchlorate, acetamide, formamide and the like. At least one of the foregoing may be used. Among these, urea is particularly preferred.

The concentration of the chaotropic agent in the pretreatment solution is not particularly limited and it is desirable that the concentration is such that when the pretreatment solution is mixed with a sample, HBs antigen is not substantially denatured. For example, when the pretreatment solution contains urea, the concentration thereof is such that when the pretreatment solution is mixed with a sample, the final concentration of urea is 0.05 to 1 M.

In an embodiment of the present invention, the temperature and duration of the treatment step may be appropriately selected according to the composition of the pretreatment solution, the type of the sample, mixing amounts of the pretreatment solution and the sample. Usually the pretreatment solution may be mixed with a sample and the mixture may be left to stand at a temperature of 15 to 25° C. for 5 to 10 minutes.

In the pretreatment method of the invention, a step (hereinafter also referred to as the "neutralizing step") of neutralizing the sample obtained from the treatment step with a reagent containing an acidic substance is carried out. In the neutralizing step, it is preferable that the sample obtained from the treatment step is mixed with the reagent containing the acidic substance such that the sample after neutralization has pH of 6.5 to 8.

In an embodiment of the present invention, the type of the acidic substance in the reagent used in the neutralizing step is not particularly limited. Examples of the acidic substance include citric acid, acetic acid, lactic acid, malic acid, succinic acid, phosphoric acid, formic acid, fumaric acid, tartaric acid, hydrochloric acid, sulfuric acid and the like. At least one of the foregoing may be used. Among these, citric acid is particularly preferred.

In an embodiment of the present invention, the concentration of the acidic substance in the reagent is not particularly limited as far as it is the concentration such that a mixture obtained by mixing the sample obtained from the treatment step with the reagent containing the acidic substance has pH of 6.5 to 8. The concentration can be appropriately selected according to the type of the acidic substance, the amount of the sample obtained from the treatment step and the like. When the acidic substance used is citric acid, the concentration of citric acid in the reagent is preferably 0.03 to 0.16 M.

In an embodiment of the present invention, the temperature and duration of the neutralizing step is not particularly limited. Usually the sample obtained from the treatment step may be mixed with the reagent containing the acidic substance and the mixture may be left to stand at a temperature of 15 to 25° C. for 1 to 10 minutes.

In an embodiment of the present invention where the pretreatment method is utilized for a method for detecting HBs antigen as described hereinafter, it is preferable that the pretreatment solution or the reagent containing the acidic substance further contains a reducing agent. With the presence of the reducing agent, aggregation of carrier particles in a step of recovering as described hereinafter can be suppressed. The reducing agent is preferably a reducing agent that can dissociate a disulfide bond of a protein. Examples of the reducing agent include mercaptoethylamine, mercaptoethanol, dithiothreitol, cysteine, dithioerythritol, sodium borohydride, phosphine and the like. Among these, mercaptoethylamine, dithiothreitol and cysteine hydrochloride are particularly preferred. In an embodiment of the present invention, the concentration of the reducing agent in the pretreatment solution or the reagent containing the acidic substance is not particularly limited as far as it does not affect the step of formation as described hereinafter. For example, when mercaptoethylamine is used, the concentration thereof is preferably 10 to 60 mM.

In an embodiment of the present invention where the pretreatment method is utilized for a method for detecting HBs antigen as described hereinafter, it is preferable that the pretreatment solution or the reagent containing the acidic substance further contains an inorganic salt. With the presence of the inorganic salt, aggregation of carrier particles in a step of recovering as described hereinafter can be suppressed. Examples of the inorganic salt include sodium chloride, potassium chloride, magnesium chloride, sodium sulfate and the like. Among these, sodium chloride, potassium chloride and sodium sulfate are particularly preferred. In an embodiment of the present invention, the concentration of the inorganic salt in the pretreatment solution or the reagent containing the acidic substance is not particularly limited as far as it does not affect the step of formation as described hereinafter. For example, when sodium chloride is used, the concentration thereof is preferably 0.1 to 1 M.

The scope of the present invention encompasses a method for detecting HBs antigen utilizing the pretreatment method of the present invention. The method for detecting HBs antigen is not particularly limited as far as it is a well-known immunoassay. The detection method of the present invention is particularly preferably an immunocomplex transfer assay comprising a "transfer step" as described hereinafter in order to detect HBs antigen with high sensitivity using the pretreatment method of the present invention. The method for detecting HBs antigen of the present invention (hereinafter also referred to as the "detection method") is hereinafter described.

In the detection method of the present invention, HBs antigen is detected through the steps described hereinafter by using a sample obtained by treating a sample suspected to contain the HBs antigen with the pretreatment method of the present invention. Therefore specific procedures and the like of the pretreatment step of a sample suspected to contain HBs antigen and the subsequent neutralizing step in the detection method of the present invention are the same as those described above for the pretreatment method of the present invention.

After the above two steps, in the detection method of the present invention, a step (hereinafter also referred to as the "step of formation") of adding to the sample obtained from the neutralizing step a labeled antibody binding to the HBs antigen, carrier particles and a first antibody binding to the HBs antigen and the carrier particles, in order to form a complex of the HBs antigen, the labeled antibody and the first antibody on the carrier particles is carried out.

In an embodiment of the present invention, a labeled antibody binding to HBs antigen (hereinafter merely referred to as the "labeled antibody") is not particularly limited as far as it can specifically bind to HBs antigen and is labeled with a well-known labeling substance conventionally used in immunological methods. The labeled antibody can be prepared by linking an anti-HBs antibody and a labeling substance by a well-known method in which an appropriate cross-linking agent or a commercially available labeling kit is used. The antibody to be labeled may be a fragment or derivative of an antigen-binding antibody such as Fab and $F(ab')_2$.

In an embodiment of the present invention, the labeling substance is not particularly limited as far as it can generate a signal that can be detected or measured. Examples of the labeling substance include enzymes, fluorescent substances, radioisotopes and the like. Examples of the enzyme include alkaline phosphatase, peroxidase, glucose oxydase, tyrosinase, acid phosphatase, luciferase and the like. Examples of the fluorescent substance include fluorescent dyes such as fluorescein isothiocyanate (FITC), fluorescent proteins such as green fluorescence protein (GFP) and the like. Examples of the radioisotope include $^{125}I$, $^{14}C$, $^{32}P$ and the like. Among these, the labeling substance is preferably an enzyme.

In an embodiment of the present invention, carrier particles may be selected from well-known particles which are conventionally used in immunological methods. Examples of the carrier particles include magnetic particles, latex particles, erythrocytes, gelatin particles and the like. Among these, magnetic particles are particularly preferred. The magnetic particles as used herein are particles containing a magnetic material as a base material. Such magnetic particles are well known in the art and examples thereof include particles containing $Fe_2O_3$ and/or $Fe_3O_4$, cobalt, nickel, ferrite, magnetite and the like as a base material.

In an embodiment of the present invention, a first antibody binding to HBs antigen and carrier particles (hereinafter merely referred to as the "first antibody") is not particularly limited as far as it specifically binds to an epitope of the HBs antigen that is different from the epitope to which the labeled antibody binds through an antigen-antibody reaction and can bind to the carrier particle. A manner of binding of the first antibody to the carrier particle is not particularly limited as far as it is dissociable and examples thereof include physical adsorption, ion binding and the like. The first antibody may bind to the carrier particle via a substance linking the antibody and the carrier particle. Such a substance is preferably a pair of substances which can specifically bind to each other and can dissociate each other (for the sake of convenience, two substances are referred to as "substance A" and "substance B"). For example, by attaching a substance A to the first antibody as a "binding site to a carrier particle" and attaching a substance B to a carrier particle, the first antibody can be bound to the carrier particle by utilizing affinity between the substance A and the substance B. Such a combination of the substance A and the substance B is well known in the art and examples thereof include an antigen (excluding HBs antigen) and an antibody thereof, a ligand and a receptor thereof, an oligonucleotide and a complement thereof, biotin (or desthiobiotin) and avidin (or streptavidin), nickel and a histidine tag, glutathione and glutathione-S-transferase and the like. A combination of an antigen and an antibody thereof is preferably a hapten and an anti-hapten antibody and biotin (or desthiobiotin) and an anti-biotin antibody (or an anti-desthiobiotin antibody). A combination of a hapten and an anti-hapten antibody is particularly preferably 2,4-dinitrophenol (DNP) and an anti-DNP antibody.

In an embodiment of the present invention, it is not particularly limited as to which of the substance A and the substance B is bound to the first antibody or the carrier particles. However, when a combination of an antigen and an antibody thereof is used, it is preferable that the antigen is attached to the first antibody and the antibody directed to the antigen is attached to the carrier particles. Methods for attaching the substances to the antibody and the carrier particles are well known in the art. For example, when attaching the antibody to biotin, a method is known in which a cross-linking agent (e.g., maleimide, N-hydroxysuccinimide) reactive with an amino or thiol group in the antibody is used. Known methods for attaching the substance to the carrier particles include physical adsorption, covalent bonding and ion bonding.

In a preferred embodiment of the present invention, the carrier particles used are carrier particles onto which a second antibody binding to the first antibody is immobilized, thereby allowing binding of the first antibody and the carrier particles through the second antibody. A manner of binding between the first antibody and the second antibody is desirably a dissociable bonding. For example, it is preferable to use a first antibody bound to a hapten (e.g., DNP) or biotin (or desthiobiotin) and carrier particles onto which a second antibody specifically binding to the hapten or biotin (or desthiobiotin) is immobilized. In this case, the second antibody that binds to the first antibody is an antibody that specifically binds to the hapten or biotin (or desthiobiotin). In a particularly preferred embodiment, a DNP-bound first antibody and carrier particles onto which an anti-DNP antibody is immobilized are used.

In the step of formation, the HBs antigen binds to the labeled antibody by an antigen-antibody reaction and the first antibody further binds thereto by an antigen-antibody reaction to form a complex containing "labeled antibody-HBs antigen-first antibody". By binding of the first antibody in the complex to the carrier particles, the complex containing "labeled antibody-HBs antigen-first antibody" is formed on the carrier particle. In a preferred embodiment of the present invention, the carrier particles used may be carrier particles onto which a second antibody is immobilized that binds to the first antibody, thereby forming a complex containing "labeled antibody-HBs antigen-first antibody-second antibody" on the carrier particle.

In an embodiment of the present invention, the amounts added of the labeled antibody, the carrier particles and the first antibody are not particularly limited and may be appropriately selected according to the amount of the sample. The labeled antibody, the first antibody and the carrier particles may be sequentially or simultaneously added to the sample. When the labeled antibody, the first antibody and the carrier particles are sequentially added, the order of addition of the labeled antibody and the first antibody is not limited, while it is preferable that the carrier particles are added after addition of the antibodies. Alternatively the first antibody may be bound to the carrier particles before the step of formation.

In an embodiment of the present invention, the temperature and duration of the reaction in the step of formation is not particularly limited. Usually, the reaction may be left to stand or gently stirred at a temperature of 20 to 45° C. for 15 to 30 minutes. When the labeled antibody, the first antibody and the carrier particles are sequentially added, a reaction time after addition of each component may be established.

In the detection method of the present invention, a step (hereinafter also referred to as the "step of recovering") of selectively recovering the carrier particles in the sample obtained from the step of formation of the complex is carried out. The sample contains, in addition to the carrier particles onto which the complex is formed, contaminants such as components of the pretreatment solution, excess labeled antibody, the first antibody and the like. In the step of recovering, the carrier particles are separated from the contaminants and recovered. Accordingly, the step of recovering allows removal of contaminants that may affect the measuring step as described hereinafter.

A method for selectively recovering the carrier particles in the sample is well known and can be appropriately selected according to the type of the carrier particles used. For example, when magnetic particles are used, the carrier particles in the sample can be selectively recovered by magnetic separation. Specifically, a magnet is approached to a wall of a container containing the sample obtained from the step of formation to immobilize magnetic particles in the sample on the wall of the container and a liquid phase is removed by aspiration, thereby selectively recovering the particles. When gelatin particles or latex particles are used, the particles may be precipitated by centrifugation and a liquid phase is removed by aspiration, thereby selectively recovering the particles.

In an embodiment of the present invention, the step of recovering can further include a step of washing the recovered carrier particles. The carrier particles may be washed by, for example, suspending the recovered carrier particles in a washing solution and then selectively recovering the carrier particles from the washing solution as described above. The washing solution is preferably a buffer that does not damage the complex formed on the carrier particles. The washing solution is particularly preferably a buffer containing a surfactant and examples thereof include TBS-T (0.05% Tween 20-containing Tris-buffered saline), PBST (0.05% Tween 20-containing phosphate buffered saline) and the like. Commercially available washing solutions may also be used such as the HISCL washing solution (available from Sysmex Corporation).

In the detection method of the present invention, a step (hereinafter also referred to as the "transfer step") of transferring the complex onto a solid phase other than the carrier particles by releasing the complex from the carrier particles obtained from the step of recovering is carried out. A method per se for releasing the complex from the carrier particles is well known in the art. For example, a method may be mentioned in which a releasing agent is used that can dissociate the binding between the first antibody obtained from the step of formation and the carrier particles. Such a releasing agent is well known in the art and may be appropriately selected according to the manner of binding between the first antibody and the carrier particles. For example, when the first antibody in the complex is bound to the carrier particles by physical adsorption, the releasing agent which is a solution containing a surfactant can be used to release the complex. In case of ion binding, a solution containing an ion can be used to release the complex.

The complex can be released wherein the first antibody is bound to the carrier particles through affinity between the substance A and the substance B as described above by using a substance that can dissociate the binding between the substance A and the substance B as a releasing agent. Such a releasing agent is also well known in the art and may be appropriately selected according to the combination of the substance A and the substance B. For example, in case of the binding between a hapten and an anti-hapten antibody, the releasing agent may be the hapten or a derivative thereof. In case of the binding between biotin (or desthiobiotin) and avidin (or streptavidin), the releasing agent may be biotin.

When the complex obtained from the step of formation binds to the carrier particles through binding between the first antibody and the second antibody, the releasing agent may be an antigen specifically recognized by the second antibody, so that the complex is released.

When the complex is released by using a releasing agent, the temperature and duration of the procedure is not particularly limited. Usually the reaction solution may be left to stand or gently stirred at a temperature of 20 to 45° C. for 3 to 8 minutes.

In the transfer step, the complex released from the carrier particles as described above is brought into contact with a solid phase other than the carrier particles in order to allow binding therebetween to transfer the complex onto the solid phase. The phrase "a solid phase other than the carrier particles" as used herein means another solid phase (hereinafter merely referred to as the "solid phase") that is different from the carrier particles which have been present after the addition thereof in the step of formation. Namely in the transfer step, re-binding of the released complex to the carrier particles which have been present after the addition thereof in the step of formation is not intended. Thus it is preferable in an embodiment of the present invention, that the complex released from the carrier particles is recovered and is brought into contact with a separately prepared solid phase. For example, a complex is released from carrier particles, and the carrier particles are then immobilized on the wall or bottom of a container in a similar manner as described for the step of recovering. Then a liquid phase containing the complex may be recovered and brought into contact with the solid phase.

In an embodiment of the present invention, the solid phase other than the carrier particles is not particularly limited as far as it can bind to the complex and can be selected from well-known solid phases that are conventionally used in immunological procedures. Examples of a material of the solid phase include latex, rubbers, polyethylene, polypropylene, polystyrene, styrene-butadiene copolymers, polyvinyl chloride, polyvinyl acetate, polyacrylamide, polymethacrylate, styrene-methacrylate copolymers, polyglycidyl methacrylate, acrolein-ethylene glycol dimethacrylate copolymers, polyvinylidene difluoride (PVDF), silicone, agarose, gelatin, erythrocytes, silica gel, glass, inactivated alumina, magnetic substances and the like. One or two or more of the foregoing in combination may be used. Examples of the shape of the solid phase include a microtiter plate, a test tube, particles and the like among which particles are particularly preferred.

In an embodiment of the present invention, a manner of binding between a solid phase and a complex is not particularly limited, but it is preferable that the solid phase binds to the complex via a substance that mediates between the first antibody in the complex and the solid phase. Examples of such a substance include a combination of the substance A and the substance B as described above. For example, the substance A may be attached to a first antibody as a "binding site to a solid phase" and the substance B may be allowed to bind to the solid phase, thereby linking the first antibody in the complex and the solid phase by affinity between the substance A and the substance B. Such a combination of the substance A and the substance B is preferably biotin (or desthiobiotin) and avidin (or streptavidin). The combination of the substance A and the substance B for binding between the first antibody and the solid phase is preferably different from the combination for binding between the first antibody and the carrier particles. Examples include using a first antibody to which DNP and biotin are attached, carrier particles on which an anti-DNP antibody is immobilized and a solid phase onto which an anti-biotin antibody is immobilized.

The temperature and duration of the procedure for the transfer of the complex to the solid phase is not particularly limited. Usually the reaction may be left to stand or gently stirred at a temperature of 20 to 45° C. for 1 to 30 minutes. Particularly when the solid phase is particles, the reaction may be left to stand or gently stirred for 1 to 5 minutes.

In the detection method of the present invention, a step (hereinafter also referred to as the "measuring step") of measuring a label of the labeled antibody in the complex on the solid phase obtained from the transfer step is carried out. The method per se for measuring a label of a labeled antibody is well known in the art. In an embodiment of the present invention, a method may be selected which is suitable for the type of a signal derived from a labeling substance used in the labeled antibody. For example, when the labeling substance is an enzyme, a signal such as light and color generated by reaction between the enzyme and a substrate therefore may be measured on a well known instrument. Examples of the measurement instrument include a spectrophotometer, a luminometer and the like.

The substrate of an enzyme may be appropriately selected from well-known substrates according to the enzyme. When the enzyme is alkaline phosphatase, examples of the substrate include chemiluminescent substrates such as CDP-Star® (disodium 4-chloro-3-(methoxyspiro[1,2-dioxetan-3,2'-(5'-chloro)tricyclo[3.3.1.1$^{3,7}$]decan]-4-yl) phenylphosphate) and CSPD® (disodium 3-(4-methoxyspiro[1,2-dioxetan-3,2-(5'-chloro)tricyclo [3.3.1.1$^{3,7}$]decan]-4-yl)phenylphosphate); luminescent substrates such as p-nitrophenyl phosphate, 5-bromo-4-chloro-3-indolyl phosphate (BCIP), 4-nitro blue tetrazolium chloride (NBT) and iodonitrotetrazolium (INT); fluorescent substrates such as 4-methylumbelliferyl phosphate (4MUP); chromogenic substrates such as 5-bromo-4-chloro-3-indolyl phosphate (BCIP), disodium 5-bromo-6-chloro-indolyl phosphate and p-nitrophenyl phosphate.

When the labeling substance is a radioisotope, a signal, i.e. radiation, may be measured on a well-known instrument such as a scintillation counter. When the labeling substance is a fluorescent substance, a signal, i.e. fluorescence, may be measured on a well-known instrument such as a fluorescence microplate reader.

In the detection method of the present invention, a step (hereinafter also referred to as the "detection step") of detecting the HBs antigen in the sample on the basis of the result from the measuring step is carried out. Specifically, when a label derived from the labeled antibody in the complex is measured in the measuring step, it means that HBs antigen is detected in a sample obtained from a subject. Adversely when the label is not measured, it means that HBs antigen is not detected in a sample obtained from a subject. In an embodiment of the present invention, it is preferable to use negative and positive controls respectively corresponding to a sample without HBs antigen (e.g. a biological sample obtained from a healthy subject) and a sample containing HBs antigen (e.g. a biological sample obtained from a patient with hepatitis B).

In an embodiment of the present invention, HBs antigen in a sample from a subject may be detected by comparing a measured value obtained from the measuring step and a pre-determined threshold. Namely when a measured value is at or higher than a threshold, it means that HBs antigen is detected in a sample obtained from a subject. Adversely when a measured value is lower than a threshold, it means that HBs antigen is not detected in a sample obtained from a subject. The threshold may be established as follows. First, a sample without HBs antigen and a sample containing HBs antigen are subjected to the detection method of the present invention up to the measuring step to generate the respective measured values. It is preferable that a plurality of the respective samples is used. The value that can distinguish a group of samples containing HBs antigen and a group of samples without HBs antigen can be established as the threshold. Examples of such a threshold include a median value that can divide a group of samples containing HBs antigen and a group of samples without HBs antigen into two equal parts.

The scope of the present invention also encompasses a pretreatment reagent kit that can be suitably used for the pretreatment method and the detection method of the present invention. The pretreatment reagent kit of the present invention (hereinafter also referred to as a "reagent kit") for detecting HBs antigen is hereinafter described.

The reagent kit of the present invention includes a first reagent containing an alkaline substance and a second reagent containing an acidic substance. The first reagent and the second reagent in the reagent kit of the present invention respectively correspond to "the pretreatment solution containing an alkaline substance" and "the reagent containing an acidic substance" used in the pretreatment method of the present invention. Thus the composition and the manner of use of the first reagent and the second reagent in the reagent kit of the present invention are the same as those described for the pretreatment solution and the reagent containing an acidic substance used in the pretreatment method of the present invention.

In another embodiment of the present invention, a reagent kit for detecting HBs antigen may be obtained by combining the pretreatment reagent kit, a reagent for detecting HBs antigen and the like. Thus the reagent kit for detecting HBs antigen of the present invention comprises:

a first reagent containing an alkaline substance;
a second reagent containing an acidic substance;
a third reagent containing a labeled antibody binding to HBs antigen;
a fourth reagent containing carrier particles;
a fifth reagent containing a first antibody binding to the HBs antigen and the carrier particles; and
a solid phase other than the carrier particles.

The "labeled antibody binding to HBs antigen" contained in the third reagent, the "carrier particles" contained in the fourth reagent, the "first antibody binding to the HBs antigen and the carrier particles" contained in the fifth reagent and the "solid phase other than the carrier particles" respectively correspond to the labeled antibody, the first antibody, the carrier particles and the solid phase used in the detection method of the present invention. Therefore the types, structures, manners of use of the labeled antibody, the first antibody, the carrier particles and the solid phase of the reagent kit for HBs detection of the present invention are the same as those described for the detection method of the present invention.

In an embodiment of the present invention, the third, fourth and fifth reagents may further contain appropriate buffers. Such a buffer is not particularly limited as far as it is a buffer having buffering action at pH 6.5 to 8 and examples thereof include phosphate buffered saline (PBS), imidazole buffer, triethanolamine hydrochloride buffer (TEA), Good buffers and the like. Examples of Good buffers include MES, Bis-Tris, ADA, PIPES, Bis-Tris-Propane, ACES, MOPS, MOPSO, BES, TES, HEPES, HEPPS, Tricine, Tris, Bicine, TAPS and the like buffers. In an embodiment of the present invention, the buffer may optionally contain well known additives such as protein stabilizers (such as BSA), preservatives (such as sodium azide and phenylmethanesulfonylfluoride), inorganic salts (such as magnesium chloride and zinc chloride).

The present invention is hereinafter more specifically described by way of Examples which do not limit the present invention.

EXAMPLES

Example 1: Investigation of the Effect of Pretreatment Using Seroconversion Panel 1. Materials
(1) Samples
The sample used was a seroconversion panel obtained from a HBV-positive patient (PHM935B: Boston Biomedica, Inc.). The seroconversion panel consists of sera regularly collected from one HBV positive patient and the sera have respectively known concentrations of HBs antibody. In the present Example, the samples are designated as serum Nos. 27 to 32. The samples of serum Nos. 30 to 32 had increased concentrations of HBs antibody and are considered to have undergone seroconversion. A positive control used was HISCL HBs Ag calibrator (HBs antigen concentration: 0.025 IU/mL: Sysmex Corporation) and a negative control used was a serum of a healthy subject (International Bioscience, Inc.).

(2) Pretreatment Solution (First Reagent)

An aqueous solution containing 0.3 N of sodium hydroxide (Nacalai Tesque, Inc.), 0.4% of Brij® 35 (Wako Pure Chemical Industries, Ltd.) and 1.2 M of urea (Kishida Chemical Co., Ltd.) was used as a pretreatment solution.

(3) Reagent Containing an Acidic Substance (Second Reagent)

An aqueous solution containing 0.11 M of citric acid (Kishida Chemical Co., Ltd.), NaCl (Manac Inc.) and 20 mM of mercaptoethylamine (Nacalai Tesque, Inc.) was used as a reagent containing an acidic substance.

(4) Labeled Antibody Reagent (Third Reagent)

Labeled antibodies used were two anti-HBs antibody fragments labeled with alkaline phosphatase (ALP) (hereinafter respectively referred to as "ALP-labeled HBs 85Fab'" and "ALP-labeled HBs 149Fab'"). The ALP-labeled HBs 149Fab' was prepared from a monoclonal antibody produced by a hybridoma deposited at the National Institute of Technology and Evaluation, Patent Microorganisms Depositary (#120 2-5-8 Kazusakamatari, Kisarazu-shi, Chiba, Japan, 292-0818) on 27 Mar. 2006 under the Accession Number of FERM BP-10583. The ALP-labeled HBs85Fab' was prepared from a monoclonal antibody produced by a hybridoma deposited at the National Institute of Technology and Evaluation, Patent Microorganisms Depositary (#122 2-5-8 Kazusakamatari, Kisarazu-shi, Chiba, Japan, 292-0818) on 13 Dec. 2012 under the Accession Number of NITE BP-1483. Specific procedures for preparation of the labeled antibody reagent are as follows. Each monoclonal antibody was digested with Pepsin and reduced to obtain Fab' fragments. ALP (Oriental Yeast Co., Ltd.) was maleimidated using EMCS (N-(6-maleimidocaproyloxy) succinimide) (Dojindo Laboratories). The fragments were mixed with the maleimidated ALP for reaction to obtain the labeled antibody. The resulting labeled antibody was diluted with a diluent (0.1 M MES (pH 6.5), 0.15 M NaCl, 1.0% BSA, 0.1% $NaN_3$, 10 mM $MgCl_2$, 1 mM $ZnCl_2$). The diluted solutions of the labeled antibodies were mixed at 1:1 to prepare a labeled antibody reagent (ALP concentration: 0.4 U/mL).

(5) Carrier Particle Reagent (Fourth Reagent)

A second antibody or an anti-DNP antibody (DNP-1753) was immobilized on magnetic particles (Micromer M: available from Micromod) to obtain carrier particles. The resulting carrier particles were diluted with a diluent (0.1 M MES (pH 6.5), 0.15 M NaCl, 0.25% BSA, 0.1% $NaN_3$) to prepare a carrier particle reagent (particle concentration: 0.5%) (hereinafter also referred to as "magnetic particle reagent"). The antibody was immobilized on the magnetic particles using Sulfo-SMCC (Pierce). The DNP-1753 antibody is a monoclonal antibody produced by a hybridoma deposited at the National Institute of Technology and Evaluation, Patent Microorganisms Depositary on 25 Nov. 2009 under the Accession Number of NITE P-845.

(6) First Antibody Reagent (Fifth Reagent)

First antibodies used were two anti-HBs antibodies modified with biotin and DNP (hereinafter respectively referred to as "Biotin/DNP-labeled HBs 1053" and "Biotin/DNP-labeled HBs 628"). The Biotin/DNP-labeled HBs 1053 was prepared from a monoclonal antibody produced by a hybridoma deposited at the National Institute of Technology and Evaluation, Patent Microorganisms Depositary on 27 Mar. 2006 under the Accession Number of FERM BP-10582. The Biotin/DNP-labeled HBs 628 was prepared from a monoclonal antibody produced by a hybridoma deposited at the National Institute of Technology and Evaluation, Patent Microorganisms Depositary on 13 Dec. 2012 under the Accession Number of NITE BP-1484. Specific procedures for preparation of the labeled antibody reagent are as follows. A biotinylation reagent (EZ-Link® Sulfo-NHS-LC-Biotin Reagents: Pierce) was added to BSA (Proliant) and then a DNP-labeling reagent (DNP-X acid SE: ABD Bioquest) was added to prepare BSA labeled with biotin and DNP (Biotin/DNP-labeled BSA). The Biotin/DNP-labeled BSA was maleimidated with EMCS (Dojindo Laboratories). Each monoclonal antibody and maleimidated Biotin/DNP-labeled BSA were mixed for reaction to obtain the first antibody. The resulting first antibody was diluted with a diluent (0.1 M MES (pH 6.5), 0.15 M NaCl, 1.0% BSA, 0.1% $NaN_3$). The diluted solutions of the antibodies were mixed at 1:1 to prepare a first antibody reagent (concentration of each antibody: 0.5 μg/mL).

(7) Releasing Agent

A releasing agent used for dissociating binding between DNP bound to the first antibody and the second antibody was a DNP-Lys solution. The DNP-Lys solution was prepared by diluting N-(2,4-dinitrophenyl)-L-lysine (Tokyo Chemical Industry Co., Ltd.) to the final concentration of 5 mM with a diluent (0.1 M MES (pH 6.5), 0.25% BSA, 0.1% $NaN_3$).

(8) Solid Phase

A solid phase other than the carrier particles used was a streptavidin-immobilized microplate (Nunc).

2. Pretreatment of Samples (1) Treatment Step

The sample (60 μL) was mixed with the pretreatment solution (50 μL) and incubated at room temperature for 7 minutes in order to treat the sample in the presence of sodium hydroxide at the final concentration of about 0.136 N.

(2) Neutralizing Step

The sample obtained from the above treatment step was mixed with the reagent containing an acidic substance (50 μL) and incubated at room temperature for 8 minutes to neutralize the sample. The neutralized sample was examined for pH with a pH test paper (Whatman), which indicated pH of 7 to 7.5.

(3) Preparation of Comparative Sample

In order to investigate the effect of pretreatment, a comparative sample was prepared which was not subjected to the treatment step and the neutralizing step. Namely each sample (60 μL) was mixed with HISCL sample dilution solution (Sysmex Corporation) (100 μL) to obtain a comparative sample.

3. Detection of HBs Antigen (1) Step of Formation

The sample (160 μL) obtained from the neutralizing step was mixed with the labeled antibody reagent (100 μL) in a reaction cuvette (reaction cuvette for HISCL: available from Sysmex Corporation) and incubated at 42° C. for 8 minutes. To the reaction cuvette, the first antibody reagent (100 μL)

was added and incubated at 42° C. for 8 minutes. To the reaction cuvette, the magnetic particle reagent (50 μL) was further added and incubated at 42° C. for 10 minutes to carry out the step of formation. The comparative sample which did not undergo the pretreatment step was also similarly processed.

(2) Step of Recovering

The reaction cuvette containing the sample obtained from the step of formation was subjected to magnetic separation on a magnetism collector (MINITUBE MAG SEPARATOR: available from SPHERO TECH) and a supernatant in the cuvette was removed to recover the carrier particles. To the reaction cuvette, a washing solution (350 μL) (HISCL washing solution: Sysmex Corporation) was added and magnetic separation was repeated to wash the carrier particles. A similar washing procedure was repeated twice to recover the carrier particles.

(3) Transfer Step

To the reaction cuvette containing the sample obtained from the step of recovering, the releasing agent (40 μL) was added and incubated at 42° C. for 5 minutes. Magnetic separation was carried out on the magnetism collector and a supernatant was recovered and transferred onto the solid phase. The solid phase was incubated at room temperature for 20 minutes to carry out the transfer step. A supernatant was removed from the solid phase to which the HISCL washing solution (300 μL) was added and a supernatant was removed again to carry out washing. A similar washing procedure was repeated 5 times.

(4) Measuring Step

To the solid phase obtained from the transfer step, the HISCL R4 reagent (17.5 μL) and the HISCL R5 reagent (17.5 μL) (Sysmex Corporation) were added and incubated at 42° C. for 5 minutes. The emission intensity (counts) was then measured on the OPTIMA (BMG LABTECH) (3 sec at gain 3960). The results of the measurements are shown in the following Table 1.

TABLE 1

| Sample | HBs antibody conc. (mIU/mL) | Emission intensity w/pretreatment (counts) | w/o pretreatment (counts) |
|---|---|---|---|
| Serum No. 27 | 0.4 | 808236 | 886043 |
| Serum No. 28 | 1.2 | 357095 | 480120 |
| Serum No. 29 | 1.8 | 149299 | 247530 |
| Serum No. 30 | 4.4 | 73167 | 153256 |
| Serum No. 31 | 26.0 | 34579 | 65578 |
| Serum No. 32 | 32.7 | 30737 | 64926 |
| Positive control | — | — | 869149 |
| Negative control | — | — | 1293 |

(5) Detection Step

The results of measurements of positive and negative controls show that the method for detecting HBs antigen of the present invention allows detection of HBs antigen in a sample. HBs antigens could be detected in samples of serum Nos. 27 to 29 which had low concentrations of HBs antibody derived from subjects even without the pretreatment method of the present invention. However, the emission intensities of the samples of serum Nos. 27 to 29, which had increased concentrations of HBs antibody, with the pretreatment method of the present invention were twice as high as the emission intensities of the samples without the pretreatment method. Accordingly the pretreatment method of the present invention eliminates effects of the HBs antibody derived from subjects to allow detection of the HBs antigen.

Reference Example 1: Investigation of the Sensitivity of the Method for Detecting HBs Antigen 1. Samples The samples used were prepared by serially diluting a serum obtained from an HBV positive patient (HBV6292-11: Zepto Metrix). The concentrations of the HBs antigen in the samples were known. In the present Example, the samples are designated as sample Nos. 7 to 12. A positive control used was HISCL HBs Ag calibrator (HBs antigen concentration: 0.025 IU/mL: Sysmex Corporation) and a negative control used was a serum of a healthy subject (International Bioscience, Inc.).

2. Investigation of Detection Sensitivity

The pretreatment and detection were carried out in similar manners as in Example 1 except that the above serum diluted solutions were used as samples to detect HBs antigen in the samples. The results are shown in the following Table 2. The "S/N ratio" in the table is calculated by the following equation.

$$(S/N \text{ ratio}) = \{(\text{emission intensity of a sample}) - (\text{emission intensity of the negative control})\} / (\text{emission intensity of the negative control})$$

TABLE 2

| Sample | HBs antigen conc. (IU/mL) | Emission intensity (counts) | S/N ratio |
|---|---|---|---|
| Sample No. 7 | 0.01478 | 70451 | 52.3 |
| Sample No. 8 | 0.00739 | 35554 | 25.9 |
| Sample No. 9 | 0.00370 | 18316 | 12.8 |
| Sample No. 10 | 0.00185 | 9707 | 6.3 |
| Sample No. 11 | 0.00092 | 5601 | 3.2 |
| Sample No. 12 | 0.00046 | 3728 | 1.8 |
| Negative control | 0 | 1323 | — |
| Positive control | 0.025 | 95864 | — |

Table 2 showed that the HBs detection method of the present invention allows detection of HBs antigen even from a sample having an amount of HBs antigen as minute as 0.00046 IU/mL. It is regarded that a method using a conventional HBs antigen detection reagent has a minimum detection sensitivity as the concentration of HBs antigen of 0.05 IU/mL. Thus it was suggested that the method for detecting HBs antigen of the present invention has about 100 times higher detection sensitivity than a method using a conventional reagent.

Reference Example 2: Investigation of Effect of Pretreatment Solution on HBs Antigen 1. Materials (1) Samples The sample used was HISCL HBs Ag calibrator (Sysmex Corporation). The concentration of the HBs antigen in the sample is known. A negative control used was a serum of a healthy subject (International Bioscience, Inc.).

(2) Pretreatment Solution

As a comparison to the pretreatment solution used in Example 1, a comparative pretreatment solution having increased concentrations of the components was prepared. Namely, an aqueous solution containing 0.5 N of sodium hydroxide (Nacalai Tesque, Inc.), 4% of Brij® 35 (Wako Pure Chemical Industries, Ltd.) and 6 M of urea (Kishida Chemical Co., Ltd.) was used as a comparative pretreatment solution.

2. Investigation of Effect on HBs Antigen

The pretreatment and detection were carried out in similar manners as in Example 1 except that the above serum was used as a sample and the pretreatment solution used was the pretreatment solution of Example 1 or the comparative pretreatment solution to detect HBs antigen in the sample. Thus in the treatment step of the pretreatment of the sample, the sample was treated in the presence of sodium hydroxide at the final concentration of 0.136 N or 0.227N. The results are shown in the following Table 3.

TABLE 3

| Pretreatment solution | HBs antigen conc. in sample (IU/mL) | Emission intensity (counts) | S/N ratio |
|---|---|---|---|
| Pretreatment solution of Ex. 1 | 0.025 | 697505 | 510 |
|  | 0 | 1365 | — |
| Comparative pretreatment solution | 0.025 | 85305 | 76 |
|  | 0 | 1103 | — |

Table 3 shows that the detection method using the comparative pretreatment solution allowed detection of HBs antigen in a sample; however the S/N ratio was significantly decreased compared to the detection method of the present invention using the pretreatment solution of Example 1. This indicates that the HBs antigen is denatured by the comparative pretreatment solution to lose antigenicity thereof. In contrast, the method for detecting HBs antigen utilizing the pretreatment method of the present invention has high S/N ratio, indicating that the effect of the pretreatment solution to the HBs antigen may be low.

Example 2: Investigation of the Effect of Pretreatment Using Seroconversion Panel (2)

1. Materials (1) Samples

The samples used were prepared by serially diluting a serum obtained from an HBV positive patient (HBV11000-9: Zepto Metrix). In the present Example, the samples are designated as sample Nos. 1 to 4. The concentrations of the HBs antigen in the samples are known. The serum obtained from the HBV positive patient was diluted with a serum of a healthy subject (containing HBs antibody at a concentration of about 23.4 mIU/mL).

Other samples used were prepared by serially diluting a serum obtained from an HBV positive patient (HBV11048-6: Zepto Metrix). In the present Example, the samples are designated as sample Nos. 5 to 8. The concentrations of the HBs antigen in the samples are known. The serum obtained from the HBV positive patient was diluted with a serum of a healthy subject (containing HBs antibody at a concentration of about 23.4 mIU/mL).

(2) Pretreatment Solution

An aqueous solution containing 0.03 N of sodium hydroxide (Nacalai Tesque, Inc.), 0.4% of Brij® 35 (Wako Pure Chemical Industries, Ltd.) and 1.2 M of urea (Kishida Chemical Co., Ltd.) was used as a pretreatment solution.

2. Pretreatment of Samples (1) Treatment Step

The sample (120 μL) was mixed with the pretreatment solution (100 μL) and incubated at room temperature for 7 minutes in order to treat the sample in the presence of sodium hydroxide at the final concentration of about 0.014 N.

(2) Neutralizing Step

The sample obtained from the above treatment step was mixed with the reagent containing an acidic substance (80 μL) as in Example 1 and incubated at room temperature for 5 minutes to neutralize the sample.

3. Detection of HBs Antigen (1) Step of Formation

The sample (300 μL) obtained from the neutralizing step was mixed with the labeled antibody reagent (100 μL) as in Example 1 in a reaction cuvette (reaction cuvette for HISCL: available from Sysmex Corporation) and incubated at 42° C. for 9 minutes. To the reaction cuvette, the first antibody reagent (100 μL) as in Example 1 was added and incubated at 42° C. for 9 minutes. To the reaction cuvette, the carrier particle reagent (75 μL) as in Example 1 was further added and incubated at 42° C. for 10 minutes to carry out the step of formation.

(2) Step of Recovering

The reaction cuvette containing the sample obtained from the step of formation was subjected to magnetic separation on a magnetism collector (MINITUBE MAG SEPARATOR: available from SPHERO TECH) and a supernatant in the cuvette was removed to recover the carrier particles. To the reaction cuvette, the washing solution was added and magnetic separation was repeated to wash the carrier particles. Washing with 600 μL of the washing solution was carried out twice and washing with 150 μL of the washing solution was carried out once. The washing solution used herein was prepared by adding NaCl to the HISCL washing solution (Sysmex Corporation) so as to adjust the concentration of NaCl to 0.4 M.

(3) Transfer Step

To the reaction cuvette containing the sample obtained from the step of recovering, the releasing agent (33 μL) as in Example 1 was added and incubated at 38° C. for 5 minutes. Magnetic separation was carried out on the magnetism collector and 33 μL of supernatant was recovered. Hereinafter the sample was processed up to the measuring step on the HISCL 2000i (available from Sysmex Corporation). Specifically, the following process was carried out on the HISCL 2000i. To the recovered supernatant, the carrier particle reagent (60 μL) as in Example 1 was added and incubated at 42° C. for about 6 minutes to carry out the transfer step. In the present Example, the magnetic particles in the carrier particle reagent added correspond to the solid phase. A supernatant was removed from the solid phase to which the washing solution (300 μL) used in the (2) step of recovering was added and a supernatant was removed again to carry out washing. A similar washing procedure was repeated 5 times.

(4) Measuring Step

To the solid phase obtained from the transfer step, the HISCL R4 reagent (50 μL) and the HISCL R5 reagent (100 μL) (Sysmex Corporation) were added and incubated at 42° C. for 5 minutes. The emission intensity (counts) was then measured. The results of the measurements are shown in the following Tables 4 and 5.

TABLE 4

| | HBs antigen concentration (IU/mL) | | | |
|---|---|---|---|---|
| | 0.00000 | 0.00020 | 0.00040 | 0.00080 |
| Sample No. 1 | 850 | 1,236 | 1,688 | 2,220 |
| Sample No. 2 | 777 | 1,178 | 1,466 | 2,557 |

TABLE 4-continued

|  | HBs antigen concentration (IU/mL) | | | |
| --- | --- | --- | --- | --- |
|  | 0.00000 | 0.00020 | 0.00040 | 0.00080 |
| Sample No. 3 | 711 | 1,267 | 1,582 | 2,432 |
| Sample No. 4 | 857 | 1,300 | 1,765 | 2,408 |
| Average (AVR) | 799 | 1,245 | 1,625 | 2,404 |
| Standard deviation (SD) | 69 | 52 | 130 | 139 |
| AVR + 2SD | 937 | 1349 | 1885 | 2682 |
| AVR − 2SD | 661 | 1141 | 1365 | 2126 |

TABLE 5

|  | HBs antigen concentration (IU/mL) | | | |
| --- | --- | --- | --- | --- |
|  | 0.00000 | 0.00020 | 0.00040 | 0.00080 |
| Sample No. 5 | 900 | 1,134 | 1,426 | 1,919 |
| Sample No. 6 | 912 | 1,293 | 1,539 | 2,064 |
| Sample No. 7 | 860 | 1,265 | 1,559 | 2,190 |
| Sample No. 8 | 886 | 1,219 | 1,539 | 2,088 |
| Average (AVR) | 890 | 1,228 | 1,516 | 2,065 |
| Standard deviation (SD) | 22 | 70 | 61 | 112 |
| AVR + 2SD | 934 | 1368 | 1638 | 2289 |
| AVR − 2SD | 846 | 1088 | 1394 | 1841 |

As shown in Tables 4 and 5, it was found by the 2SD method that the HBs detection method of the present invention allows detection of HBs antigen even in the HBs antibody-containing sample prepared from the seroconversion panel having an amount of HBs antigen as minute as 0.0002 IU/mL.

Example 3: Investigation of Effect of Difference in Concentration of Alkaline Substance in Pretreatment Solution on Sensitivity of HBs Antigen 1. Materials
(1) Samples The samples used were three sera obtained from HBV positive patients (HBV6290-6, HBV11048-6 and HBV6272-6: all from Zepto Metrix).

(2) Pretreatment Solution
(i) Pretreatment Solution 1

An aqueous solution containing 0.15 N of sodium hydroxide (Nacalai Tesque, Inc.), 0.4% of Brij® 35 (Wako Pure Chemical Industries, Ltd.) and 1.2 M of urea (Kishida Chemical Co., Ltd.) was used as pretreatment solution 1.

(ii) Pretreatment Solution 2

An aqueous solution containing 0.625 N of sodium hydroxide (Nacalai Tesque, Inc.), 0.4% of Brij® 35 (Wako Pure Chemical Industries, Ltd.) and 1.2 M of urea (Kishida Chemical Co., Ltd.) was used as pretreatment solution 2.

2. Pretreatment of Samples
(1) Treatment Step

The sample (120 µL) was mixed with pretreatment solution 1 (100 µL) and incubated at room temperature for 7 minutes in order to treat the sample in the presence of sodium hydroxide at the final concentration of about 0.06 N. The same sample was subjected to the same procedure except that pretreatment solution 2 was used instead of pretreatment solution 1. Thus the sample (120 µL) was mixed with pretreatment solution 2 (80 µL) and incubated at room temperature for 7 minutes in order to treat the sample in the presence of sodium hydroxide at the final concentration of about 0.25 N.

(2) Neutralizing Step

The sample obtained from the above treatment step was mixed with the reagent containing an acidic substance (80 µL) as in Example 1 and incubated at room temperature for 5 minutes to neutralize the sample.

3. Detection of HBs Antigen
(1) Step of Formation

The sample (300 µL) obtained from the neutralizing step was mixed with the labeled antibody reagent (100 µL) as in Example 1 in a reaction cuvette (reaction cuvette for HISCL: available from Sysmex Corporation) and incubated at 42° C. for 9 minutes. To the reaction cuvette, the first antibody reagent (100 µL) as in Example 1 was added and incubated at 42° C. for 9 minutes. To the reaction cuvette, the carrier particle reagent (75 µL) as in Example 1 was further added and incubated at 42° C. for 10 minutes to carry out the step of formation.

(2) Step of Recovering

The reaction cuvette containing the sample obtained from the step of formation was subjected to magnetic separation on a magnetism collector (MINITUBE MAG SEPARATOR: available from SPHERO TECH) and a supernatant in the cuvette was removed to recover the carrier particles. To the reaction cuvette, the washing solution was added and magnetic separation was repeated to wash the carrier particles. Washing with 600 µL of the washing solution was carried out twice and washing with 150 µL of the washing solution was carried out once. The washing solution used herein was prepared by adding NaCl to the HISCL washing solution (Sysmex Corporation) so as to adjust the concentration of NaCl to 0.4 M.

(3) Transfer Step

To the reaction cuvette containing the sample obtained from the step of recovering, the releasing agent (33 µL) as in Example 1 was added and incubated at 38° C. for 5 minutes. Magnetic separation was carried out on the magnetism collector and 33 µL of supernatant was recovered. Hereinafter the sample was processed up to the measuring step on the HISCL 2000i (available from Sysmex Corporation). Specifically, the following process was carried out on the HISCL 2000i. To the recovered supernatant, the carrier particle reagent (60 µL) as in Example 1 was added and incubated at 42° C. for about 6 minutes to carry out the transfer step. In the present Example, the magnetic particles in the carrier particle reagent added correspond to the solid phase. A supernatant was removed from the solid phase to which the washing solution (300 µL) used in the (2) step of recovering was added and a supernatant was removed again to carry out washing. A similar washing procedure was repeated 5 times.

(4) Measuring Step

To the solid phase obtained from the transfer step, the HISCL R4 reagent (50 µL) and the HISCL R5 reagent (100 µL) (Sysmex Corporation) were added and incubated at 42° C. for 5 minutes. The emission intensity (counts) was then measured. The sample treated with pretreatment solution 2 was also subjected to the same detection procedure as the sample treated with pretreatment solution 1. The results of the measurements are shown in FIGS. 1 to 3.

Figure 1:
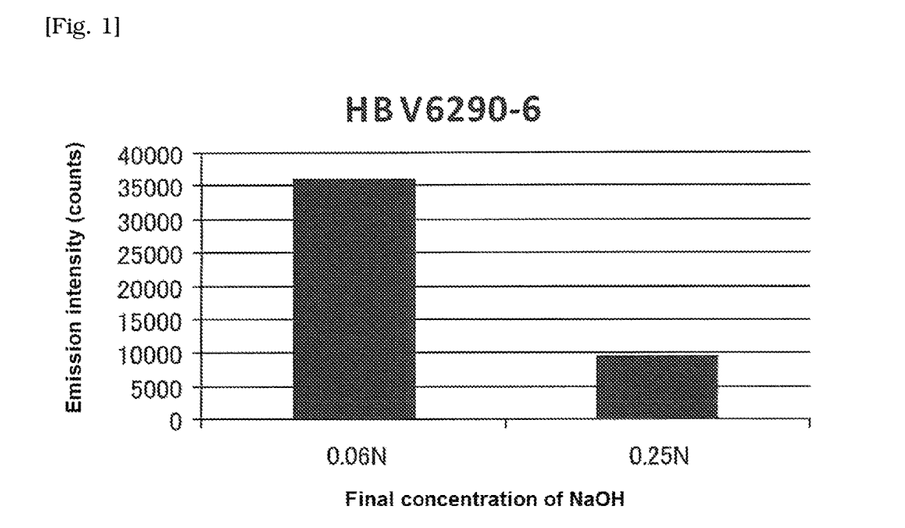
FIG. 1 is a graph showing the results (emission intensity) of detection of HBs antigen in a serum of a HBV positive patient (HBV6290-6) with a labeled antibody after pretreating the serum in the presence of an alkaline substance.
Figure 2:
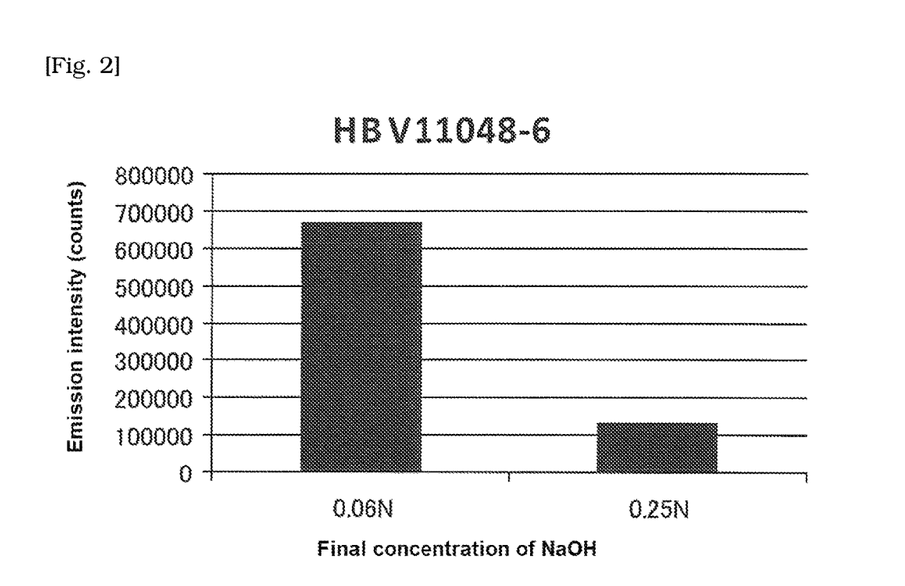
FIG. 2 is a graph showing the results (emission intensity) of detection of HBs antigen in a serum of a HBV positive patient (HBV11048-6) with a labeled antibody after pretreating the serum in the presence of an alkaline substance.
Figure 3:
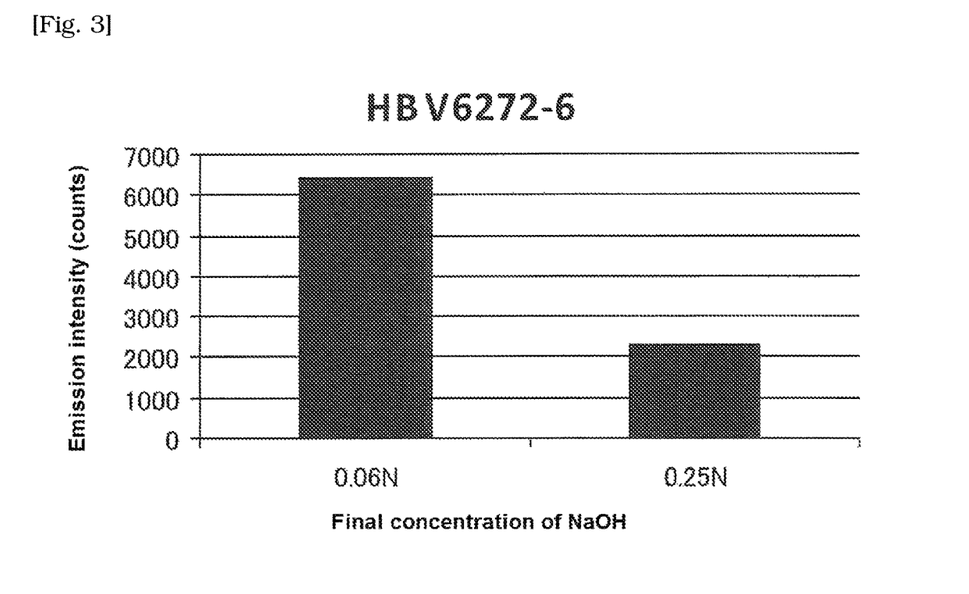
FIG. 3 is a graph showing the results (emission intensity) of detection of HBs antigen in a serum of a HBV positive patient (HBV6272-6) with a labeled antibody after pretreating the serum in the presence of an alkaline substance.

From FIGS. 1 to 3, it was found that the method for detecting HBs antigen of the present invention using pretreatment solution 1 resulted in an emission intensity that was 2.5 times or more higher than that obtained by the method for detecting HBs antigen using pretreatment solution 2 having a high concentration of an alkaline substance.

Thus it was found that the method for detecting HBs antigen of the present invention allows detection of the HBs antigen with an increased sensitivity.

What is claimed is:

1. A method for pretreating a sample to be subjected to an HBs antigen detection assay, comprising the steps of:
   (a) mixing a sample suspected to contain HBs antigen with a pretreatment solution containing an alkaline substance, so that the final concentration of the alkaline substance in the mixture is 0.012 to 0.15 N; and
   (b) neutralizing the mixture obtained in step (a) with a reagent containing an acidic substance,
   thereby pretreating said sample to be subjected to an HBs antigen detection assay,
   wherein the pretreatment solution further comprises at least one selected from the group consisting of a nonionic surfactant and a chaotropic agent.

2. The method according to claim 1, wherein the alkaline substance is a strong base.

3. The method according to claim 2, wherein the strong base is at least one selected from hydroxides, hydrides and amides of alkali metals and alkaline earth metals.

4. The method according to claim 2, wherein the strong base is at least one selected from sodium hydroxide, potassium hydroxide and magnesium hydroxide.

5. The method according to claim 1, wherein the pretreatment solution comprises a nonionic surfactant.

6. The method according to claim 5, wherein the nonionic surfactant is a polyoxyethylene nonionic surfactant.

7. The method according to claim 1, wherein the pretreatment solution comprises a chaotropic agent.

8. The method according to claim 7, wherein the chaotropic agent is at least one selected from urea, guanidine hydrochloride, sodium salicylate, sodium thiocyanate, sodium perchlorate, acetamide and formamide.

9. The method according to claim 1, wherein the acidic substance is at least one selected from citric acid, acetic acid, lactic acid, malic acid, succinic acid, phosphoric acid, formic acid, fumaric acid, tartaric acid, hydrochloric acid and sulfuric acid.

10. The method according to claim 2, wherein
    the carrier particles are particles onto which a second antibody binding to the first antibody is immobilized;
    the step of formation is the step of forming a complex comprising the HBs antigen, the labeled antibody, the first antibody and the second antibody on the carrier particles; and
    the transfer step is the step of transferring the complex of the HBs antigen, the labeled antibody and the first antibody onto a solid phase other than the carrier particles by dissociating the binding between the first antibody and the second antibody and releasing the complex.

11. The method according to claim 1, wherein the sample is at least one selected from whole blood, plasma, serum, lymph fluid, bone marrow aspirate, bile, a gastrointestinal secretion, semen, saliva, breast milk, urine, and feces.

12. The method according to claim 1, wherein the pretreatment solution contains 0.024 to 0.3 N of the alkaline substance.

13. The method according to claim 1, wherein said sample and said pretreatment solution are mixed at a 1:1 to 1:0.5 volumetric ratio.

14. The method according to claim 1, wherein the neutralized mixture produced in step (b) has a pH of 6.5 to 8.

15. The method according to claim 8, wherein the chaotropic agent is urea.

16. The method according to claim 15, wherein the mixture produced in step (a) contains 0.05 to 1 M of urea.

17. The method according to claim 9, wherein the acidic substance is citric acid.

18. The method according to claim 17, wherein said reagent contains 0.03 to 0.16 M citric acid.

19. The method according to claim 1, wherein at least one of said pretreatment solution and said reagent contains a reducing agent.

20. The method according to claim 1, wherein at least one of said pretreatment solution and said reagent contains an inorganic salt.

21. A method for pretreating a sample to be subjected to an HBs antigen detection assay, comprising the steps of:
    (a) preparing a first mixture, said first mixture being a mixture comprising a sample suspected to contain HBs antigen, and a pretreatment solution containing an alkaline substance, said first mixture containing 0.012 to 0.15 N of said alkaline substance; and
    (b) preparing a second mixture, said second mixture being a mixture comprising said first mixture and a reagent containing an acidic substance, said second mixture having a pH of 6.5 to 8,
    thereby pretreating said sample to be subjected to an HBs antigen detection assay.

22. The method according to claim 2, wherein the pretreatment solution further comprises a nonionic surfactant.

23. The method according to claim 22, wherein the nonionic surfactant is a polyoxyethylene nonionic surfactant.

* * * * *